(12) United States Patent
Burkett et al.

(10) Patent No.: US 10,772,564 B2
(45) Date of Patent: Sep. 15, 2020

(54) INTRAVASCULAR DEVICES, SYSTEMS, AND METHODS HAVING SEPARATE SECTIONS WITH ENGAGED CORE COMPONENTS

(71) Applicant: Koninklijke Philips N.V., Amsterdam (NL)

(72) Inventors: David Burkett, Temecula, CA (US); Eric Henderson, Temecula, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 483 days.

(21) Appl. No.: 14/692,443

(22) Filed: Apr. 21, 2015

(65) Prior Publication Data

US 2015/0297138 A1    Oct. 22, 2015

Related U.S. Application Data

(60) Provisional application No. 61/982,080, filed on Apr. 21, 2014.

(51) Int. Cl.
*A61B 5/02*     (2006.01)
*A61B 5/00*     (2006.01)
(Continued)

(52) U.S. Cl.
CPC ............ *A61B 5/6851* (2013.01); *A61B 5/027* (2013.01); *A61B 5/0215* (2013.01); *A61B 2562/12* (2013.01); *A61B 2562/227* (2013.01)

(58) Field of Classification Search
CPC ..... A61B 5/6851; A61B 5/0215; A61B 5/027; A61B 2562/12; A61B 2562/227
See application file for complete search history.

(56) References Cited

U.S. PATENT DOCUMENTS

| | | |
|---|---|---|
| 4,691,709 A | 9/1987 | Cohen |
| 5,125,137 A | 6/1992 | Corl |

(Continued)

FOREIGN PATENT DOCUMENTS

| | | |
|---|---|---|
| EP | 2298162 | 3/2011 |
| JP | 2005514115 A | 5/2005 |

(Continued)

OTHER PUBLICATIONS

Korean Intellectual Property Office, International Search Report for PCT/US2015/026643 dated Jul. 27, 2015, 13 pages.
(Continued)

*Primary Examiner* — Navin Natnithithadha
*Assistant Examiner* — Andrey Shostak

(57) ABSTRACT

Intravascular devices, systems, and methods are disclosed. In some instances, the intravascular device is a guide wire that includes separate sections with engaged core components. For example, a sensing guide wire can include a proximal portion having a proximal core member and at least one proximal electrical conductor and a distal portion coupled to the proximal portion, the distal portion having a distal core member, a sensing element, and at least one distal electrical conductor coupled to the sensing element, wherein engagement structures of the proximal and distal core members are engaged and wherein the at least one distal electrical conductor is coupled to the at least one proximal electrical conductor such that the at least one proximal electrical conductor is in electrical communication with the sensing element. Methods of making, manufacturing, and/or assembling such intravascular devices and associated systems are also provided.

21 Claims, 10 Drawing Sheets

(51) Int. Cl.
*A61B 5/0215* (2006.01)
*A61B 5/027* (2006.01)

(56) References Cited

U.S. PATENT DOCUMENTS

| | | | |
|---|---|---|---|
| 5,240,437 A | 8/1993 | Christian | |
| 5,873,835 A | 2/1999 | Hasting | |
| 6,090,050 A | 7/2000 | Akerfeldt et al. | |
| 6,090,052 A | 7/2000 | Akerfeldt | |
| 6,106,476 A | 8/2000 | Corl et al. | |
| 6,112,598 A * | 9/2000 | Tenerz | A61B 5/0215 73/756 |
| 6,248,082 B1 * | 6/2001 | Jafari | A61M 25/09 600/434 |
| 6,290,656 B1 | 9/2001 | Boyle | |
| 6,354,999 B1 | 3/2002 | Dgany et al. | |
| 6,551,250 B2 | 4/2003 | Khalil | |
| 6,702,762 B2 | 3/2004 | Jafari et al. | |
| 2002/0068944 A1 * | 6/2002 | White | A61B 17/22031 606/114 |
| 2004/0176683 A1 | 9/2004 | Whitin et al. | |
| 2004/0181176 A1 * | 9/2004 | Jafari | A61M 25/09 600/585 |
| 2005/0000294 A1 * | 1/2005 | Tenerz | A61B 5/6851 73/727 |
| 2006/0052700 A1 | 3/2006 | Svanerudh | |
| 2006/0074318 A1 * | 4/2006 | Ahmed | A61B 5/02158 600/465 |
| 2006/0106321 A1 | 5/2006 | Lewinsky et al. | |
| 2006/0122537 A1 * | 6/2006 | Reynolds | A61L 31/022 600/585 |
| 2007/0060822 A1 | 3/2007 | Alpert et al. | |
| 2007/0100239 A1 | 5/2007 | Nair et al. | |
| 2007/0255145 A1 * | 11/2007 | Smith | A61B 5/0215 600/485 |
| 2008/0077050 A1 * | 3/2008 | Von Malmborg | A61B 5/6851 600/585 |
| 2008/0139951 A1 | 6/2008 | Patangay et al. | |
| 2010/0234698 A1 | 9/2010 | Manstrom et al. | |
| 2011/0166519 A1 * | 7/2011 | Nguyen | A61N 1/403 604/114 |
| 2011/0306961 A1 | 12/2011 | Turovskiy et al. | |
| 2013/0237864 A1 | 9/2013 | Mazar et al. | |
| 2013/0253374 A1 * | 9/2013 | Simpson | A61M 25/09 600/585 |
| 2013/0296692 A1 * | 11/2013 | Vanney | A61M 25/09 600/424 |
| 2014/0005543 A1 | 1/2014 | Burkett | |
| 2014/0180141 A1 | 6/2014 | Miller | |
| 2014/0187874 A1 | 7/2014 | Burkett | |
| 2014/0187980 A1 | 7/2014 | Burkett | |
| 2014/0187984 A1 | 7/2014 | Burkett | |

FOREIGN PATENT DOCUMENTS

| | | |
|---|---|---|
| JP | 2011166519 A | 8/2011 |
| WO | WO 2000/053081 | 9/2000 |
| WO | WO 2001/013779 | 3/2001 |
| WO | 2007145751 A2 | 12/2007 |
| WO | WO 2012/093260 | 7/2012 |
| WO | WO 2012/093266 | 7/2012 |
| WO | WO 2013/028612 | 2/2013 |

OTHER PUBLICATIONS

The International Bureau of WIPO, Written Opinion of the International Searching Authority, Search Report for PCT/GB2012/050024, dated Apr. 19, 2012, 15 pages.
The International Bureau of WIPO, Written Opinion of the International Searching Authority, Search Report for PCT/GB2012/050015, dated Apr. 20, 2012, 14 pages.
The International Bureau of WIPO, Written Opinion of the International Searching Authority, Search Report for PCT/US2012/051566, dated Mar. 29, 2013, 9 pages.
The International Bureau of WIPO, International Preliminary Report on Patentability for PCT/GB2012/050015, dated Jul. 10, 2013, 1 page.
The International Bureau of WIPO, International Preliminary Report on Patentability for PCT/GB2012/050024, dated Jul. 10, 2013, 1 page.
The International Bureau of WIPO, International Preliminary Report on Patentability for PCT/US2012/051566, dated Feb. 25, 2014, 1 page.
Davies, J. E., Evidence of a Dominant Backward-Propagating Suction Wave Responsible for Disastolic Coronary Filling in Humans, Attenuated in Left Ventricular Hypertrophy, vol. 113, No. 14, Apr. 11, 2006, pp. 1768-1778.

* cited by examiner

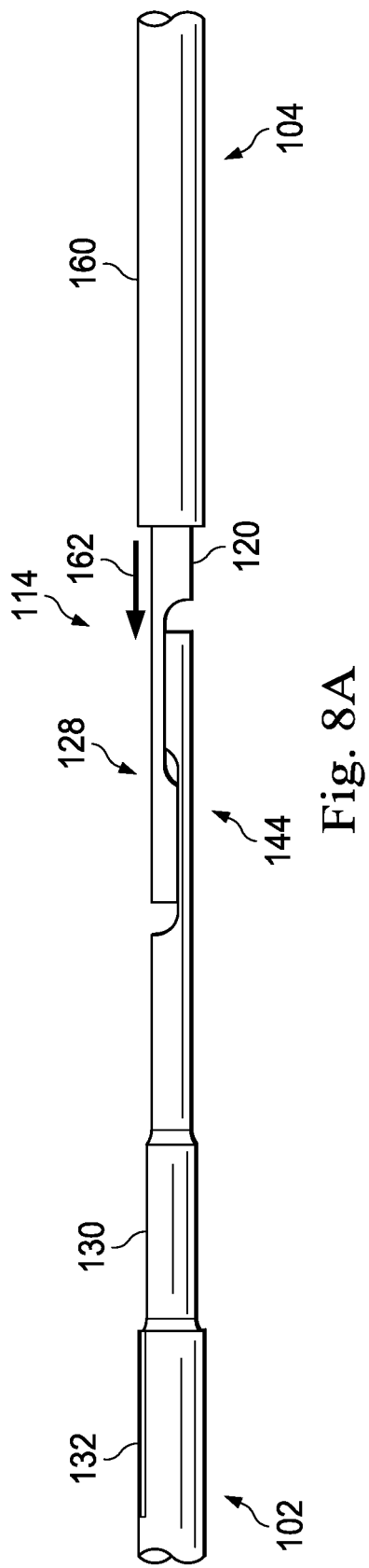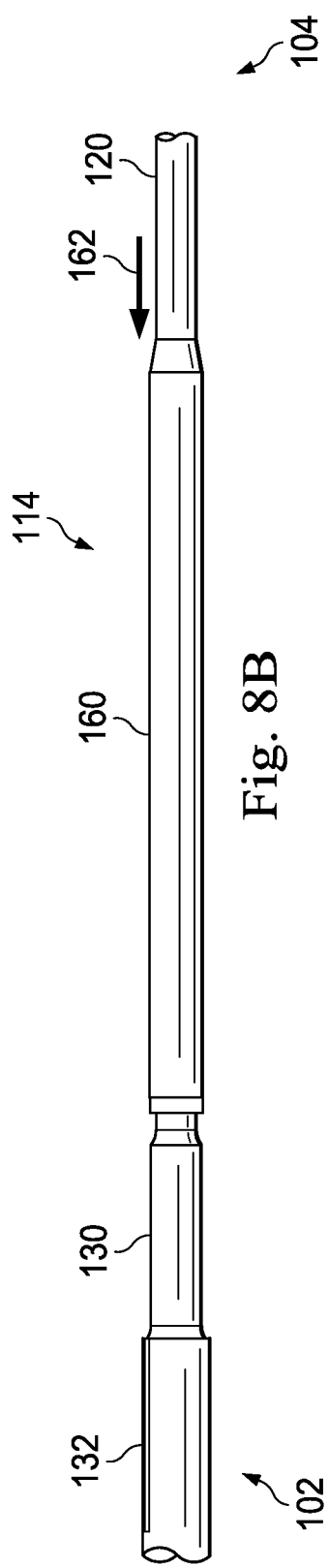
Fig. 8A
Fig. 8B

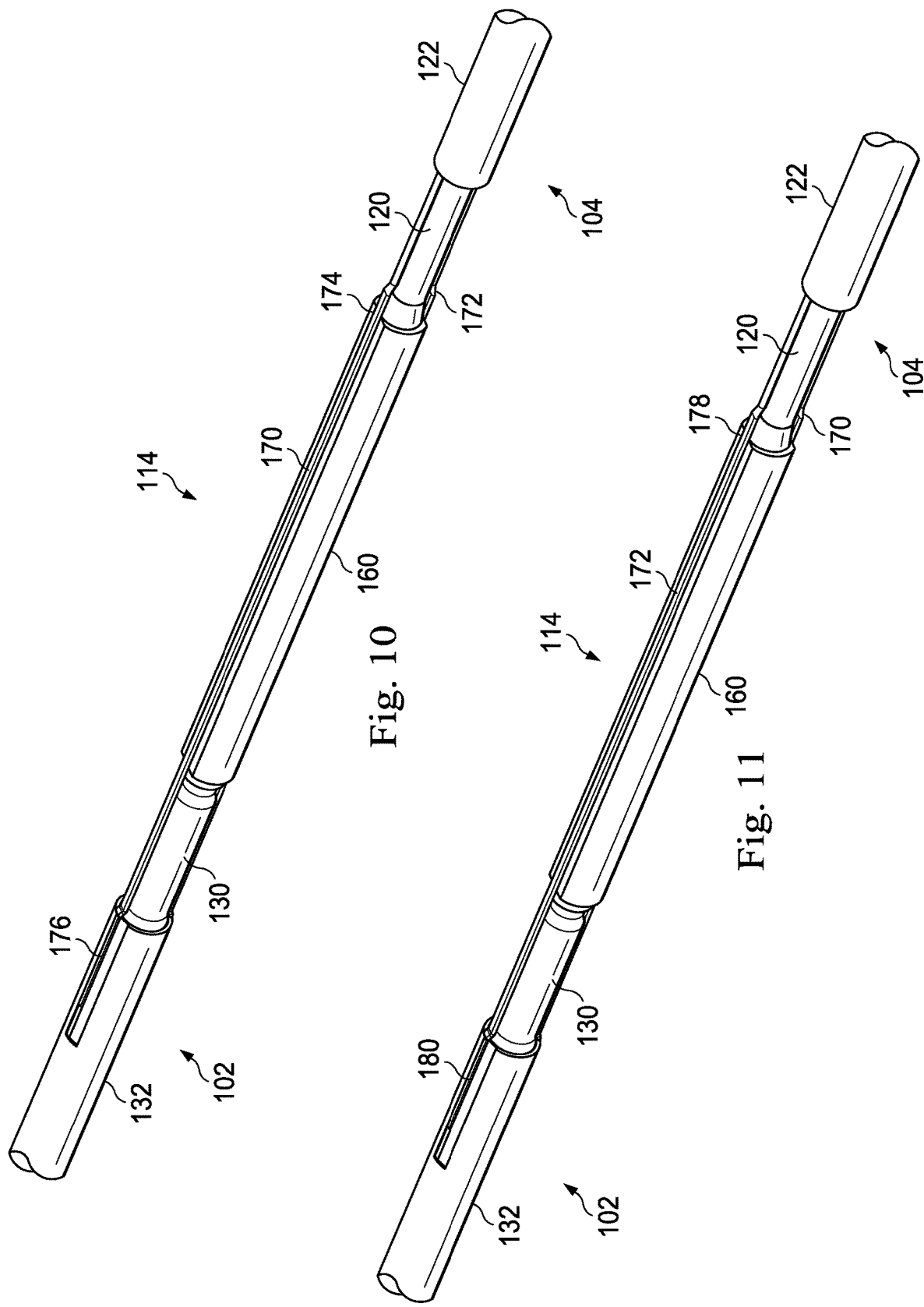

INTRAVASCULAR DEVICES, SYSTEMS, AND METHODS HAVING SEPARATE SECTIONS WITH ENGAGED CORE COMPONENTS

CROSS REFERENCE TO RELATED APPLICATIONS

The present application claims priority to and the benefit of the U.S. Provisional Patent Application No. 61/982,080, filed Apr. 21, 2014, which is hereby incorporated by reference in its entirety.

TECHNICAL FIELD

The present disclosure relates to intravascular devices, systems, and methods. In some embodiments, the intravascular devices are guide wires that include separate sections with engaged core components.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guide wires are utilized to measure the pressure within the blood vessel, visualize the inner lumen of the blood vessel, and/or otherwise obtain data related to the blood vessel. To date, guide wires containing pressure sensors, imaging elements, and/or other electronic, optical, or electro-optical components have suffered from reduced performance characteristics compared to standard guide wires that do not contain such components. For example, the handling performance of previous guide wires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guide wire. Further, due to its small diameter, in many instances the proximal connector portion of the guide wire (i.e., the connector(s) that facilitate communication between the electronic component(s) of the guide wire and an associated controller or processor) is fragile and prone to kinking, which can destroy the functionality of the guide wire. For this reason, surgeons are reluctant to remove the proximal connector from the guide wire during a procedure for fear of breaking the guide wire when reattaching the proximal connector. Having the guide wire coupled to the proximal connector further limits the maneuverability and handling of the guide wire.

Further, a problem with existing pressure and flow guide wires is that they require a complex assembly of many discrete components. That complex assembly process has limitations on design performance of the guide wire. The use of separate conductive wires running down the length of the wire reduces the space available for more supportive cores and can result in numerous issues during use due to poor solder joints with conductive bands, electrical shorts due to insulation issues, and breakage of the delicate conductive wires.

Accordingly, there remains a need for improved intravascular devices, systems, and methods that include one or more electronic, optical, or electro-optical components.

SUMMARY

The present disclosure is directed to intravascular devices, systems, and methods that include a guide wire having a separate sections coupled together by engaging core components.

The present disclosure provides a more robust sensing guide wire that avoids the assembly and performance issues of prior sensing guide wires. Guide wires of the present disclosure have one or more transition sections that facilitate coupling of different portions of the guide wire. Any type of sensor can be connected to guide wires of the present disclosure. In certain embodiments, only a single sensor is connected to the guide wire. In other embodiments, multiple sensors are connected to the guide wire. All of the sensors may be the same. Alternatively, the sensors may differ from each other and measure different characteristics inside a vessel. Exemplary sensors are pressure, flow, and temperature sensors. Generally, any type of pressure sensor may be used with the guide wires of the present disclosure, including piezoresistive, optical and/or combinations thereof. In certain embodiments, the pressure sensor includes a crystalline semi-conductor material. Similarly, any type of flow sensor may be used with guide wires of the present disclosure. In certain embodiments, the flow sensor includes an ultrasound transducer, such as a Doppler ultrasound transducer. The guide wire can include both a pressure sensor and a flow sensor.

Another aspect of the present disclosure provides methods for manufacturing and/or assembling an intravascular device. The methods can include providing a proximal portion having a proximal core member and at least one proximal electrical conductor, wherein a distal section of the proximal core member includes a first engagement structure; providing a distal portion having a distal core member, a sensing element, and at least one distal electrical conductor coupled to the sensing element, wherein a proximal section of the distal core member includes a second engagement structure; and coupling the proximal portion to the distal portion, including: securing the proximal core member to the distal core member, wherein securing the proximal core member to the distal core member includes engaging the first engagement structure with the second engagement structure; and electrically coupling the at least one proximal electrical conductor to the at least one distal electrical conductor such that the at least one proximal electrical conductor is in electrical communication with the sensing element.

In another aspect, sensing guide wires are provided. The guide wires can include a proximal portion having a proximal core member and at least one proximal electrical conductor and a distal portion coupled to the proximal portion, the distal portion having a distal core member, a sensing element, and at least one distal electrical conductor coupled to the sensing element, wherein engagement structures of the proximal and distal core members are engaged and wherein the at least one distal electrical conductor is coupled to the at least one proximal electrical conductor such that the at least one proximal electrical conductor is in electrical communication with the sensing element.

Another aspect of the present disclosure provides methods for measuring a characteristic inside a vessel. The methods can include providing a sensing guide wire in accordance with the present disclosure, inserting the guide wire into a vessel, and utilizing one or more sensing elements of the guide wire to measure one or more characteristics inside the vessel.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 8A is a side view of the components of the transition section of an intravascular device of FIG. 7 shown in arrangement according to an embodiment of the present disclosure.

FIG. 8B is a side view of the components of the transition section of an intravascular device of FIG. 7 shown in another arrangement according to an embodiment of the present disclosure.

FIG. 10 is a perspective view of components of a transition section of an intravascular device according to an embodiment of the present disclosure.

FIG. 11 is a perspective view of components of a transition section of an intravascular device according to an embodiment of the present disclosure.

DETAILED DESCRIPTION

Figure 1:
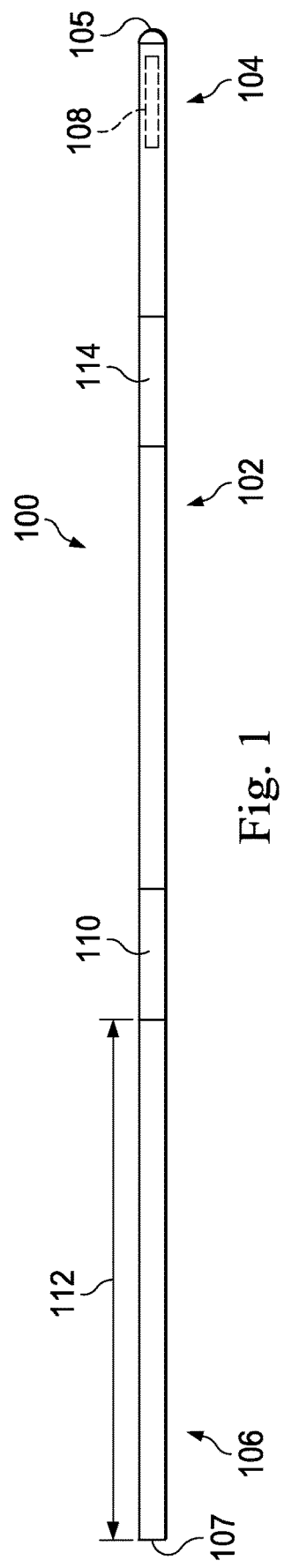
FIG. 1 is a diagrammatic, schematic side view of an intravascular device according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a flow sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guide wire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm), approximately 0.018" (0.4572 mm), and approximately 0.035" (0.889 mm). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is a portion of an intravascular device 100 according to an embodiment of the present disclosure. In that regard, the intravascular device 100 includes a flexible elongate member having a central portion 102, a distal portion 104 adjacent a distal end 105, and a proximal portion 106 adjacent a proximal end 107. A component 108 is positioned within the distal portion 104 proximal of the distal tip 105. Generally, the component 108 is representative of one or more electronic, optical, or electro-optical components. In that regard, the component 108 is a pressure sensor, a flow sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device. In some instances, the component 108 is positioned less than 10 cm, less than 5, or less than 3 cm from the distal tip 105. In some instances, the component 108 is positioned within a housing of the flexible elongate member 102. In that regard, the housing is a separate component secured to other components of the distal portion 104 in some instances. In other instances, the housing is integrally formed as a part of a component of the distal portion 104.

The intravascular device 100 also includes a connector 110 adjacent the proximal portion 106 of the device. In that regard, the connector 110 is spaced from the proximal end 107 of the intravascular device 100 by a distance 112. Generally, the distance 112 is between 0% and 50% of the total length of the intravascular device 100. While the total length of the intravascular device can be any length, in some embodiments the total length is between about 1300 mm and about 4000 mm, with some specific embodiments have a length of 1400 mm, 1900 mm, and 3000 mm. Accordingly, in some instances the connector 110 is positioned at the proximal end 107. In other instances, the connector 110 is spaced from the proximal end 107. For example, in some instances the connector 110 is spaced from the proximal end 107 between about 0 mm and about 1400 mm. In some specific embodiments, the connector 110 is spaced from the proximal end by a distance of 0 mm, 300 mm, and 1400 mm.

The connector 110 is configured to facilitate communication between the intravascular device 100 and another device. More specifically, in some embodiments the connector 110 is configured to facilitate communication of data obtained by the component 108 to another device, such as a computing device or processor. Accordingly, in some embodiments the connector 110 is an electrical connector. In such instances, the connector 110 provides an electrical connection to one or more electrical conductors that extend along the length of the flexible elongate member 102 and are electrically coupled to the component 108. In other embodiments, the connector 110 is an optical connector. In such instances, the connector 110 provides an optical connection to one or more optical communication pathways (e.g., fiber optic cable) that extend along the length of the flexible elongate member 102 and are optically coupled to the component 108. Further, in some embodiments the connector 110 provides both electrical and optical connections to both electrical conductor(s) and optical communication pathway(s) coupled to the component 108. In that regard, it should be noted that component 108 is comprised of a plurality of elements in some instances. The connector 110 is configured to provide a physical connection to another device, either directly or indirectly. In some instances, the connector 110 is configured to facilitate wireless communication between the intravascular device 100 and another device. Generally, any current or future developed wireless protocol(s) may be utilized. In yet other instances, the connector 110 facilitates both physical and wireless connection to another device.

As noted above, in some instances the connector 110 provides a connection between the component 108 of the intravascular device 100 and an external device. Accordingly, in some embodiments one or more electrical conductors, one or more optical pathways, and/or combinations thereof extend along the length of the intravascular device 100 between the connector 110 and the component 108 to facilitate communication between the connector 110 and the component 108. Generally, any number of electrical conductors, optical pathways, and/or combinations thereof can extend along the length of the intravascular device 100 between the connector 110 and the component 108. In some instances, between one and ten electrical conductors and/or optical pathways extend along the length of the intravascular device 100 between the connector 110 and the component 108. The number of communication pathways and the number of electrical conductors and optical pathways is determined by the desired functionality of the component 108 and the corresponding elements that define component 108 to provide such functionality.

Figure 2:
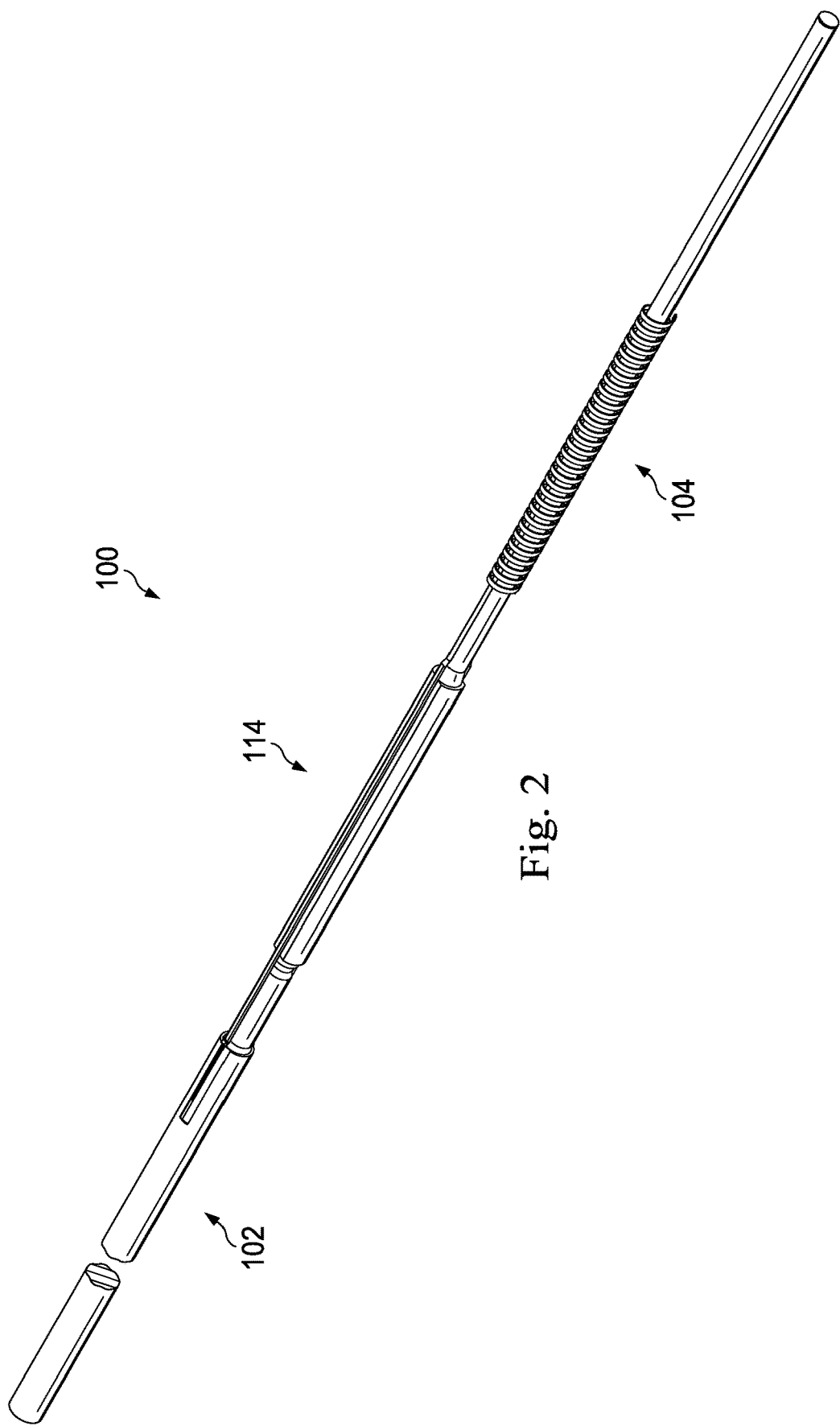
FIG. 2 is a perspective view of a transition section of an intravascular device according to an embodiment of the present disclosure.

As shown in FIGS. 1 and 2, the intravascular device 100 includes a transition section 114 where the central portion 102 is coupled to the distal portion 104. FIGS. 3-15 described below discuss various features of the transition section 114 in accordance with the present disclosure. In that regard, it is understood that the features described below for coupling the central portion 102 and the distal portion 104 may be similarly applied to couple any two parts of the intravascular device 100 together, including (1) coupling any two of the central portion 102, the distal portion 104, and/or the proximal portion 106 together, (2) coupling two or more sections together that collectively define the central portion 102, the distal portion 104, and/or the proximal portion 106; and/or (3) combinations of (1) and (2). While the following description will focus on features of the transition section 114 in the context of a specific example of the central portion 102 and a specific example of the distal portion 104, no limitation is intended thereby. Instead, it is understood that the concepts of the present disclosure are applicable to intravascular devices having various types of proximal, distal, and central portions. In some particular instances, the transition section is utilized to couple two or more parts, components, sections, and/or portions similar to those described in one or more of U.S. Pat. Nos. 5,125,137; 5,873,835; 6,106,476; 6,551,250; and U.S. patent application Ser. No. 13/931,052, published as U.S. Patent Application Publication No. 2014/0005543 on Jan. 2, 2014, U.S. patent application Ser. No. 14/135,117, published as U.S. Patent Application Publication No. 2014/0180141 on Jun. 26, 2014, U.S. patent application Ser. No. 14/137,364, published as U.S. Patent Application Publication No. 2014/0187980 on Jul. 3, 2014, and U.S. patent application Ser. No. 14/139,543, published as U.S. Patent Application Publication No. 2014/0187984 on Jul. 3, 2014, U.S. patent application Ser. No. 14/143,304, published as U.S. Patent Application Publication No. 2014/0187874 on Jul. 3, 2014, and U.S. Provisional Patent Application No. 61/935,113, filed Feb. 3, 2014, each of which is hereby incorporated by reference in its entirety.

Referring now to FIGS. 3-15, shown therein are aspects of the transition section(s) of the intravascular devices of the present disclosure. In that regard, one of the major issues associated with existing functional guide wires is poor mechanical performance as compared to frontline guide wires. The transition section(s) of the present disclosure facilitate (1) intravascular devices having improved mechanical performance; (2) selection of the best performance core material(s) for different portions of the intravascular device; (3) a simplified manufacturing process that allows for (a) one or more portions of the intravascular device to be completely assembled and tested as a functional unit prior to attachment to the other portion(s) of the intravascular device, (b) the use of shorter, individual portions that reduce the working space needed for assembly, and (c) reduction of the amount, and corresponding cost, of core wire and other components that are scrapped during typical assembly; (4) the creation of a family of intravascular devices where the particular portions/sections used to form the intravascular device may be selected and coupled together using one or more transition sections based on the desired functionality of the intravascular device; (5) minimizing the amount of handling of each portion/section throughout the build process because the different portion/section can be manufactured/assembled separately and then coupled together; and (6) simplifying the electrical/optical connection process utilized to connect communication pathways between portions/sections by utilizing a uniform approach.

Figure 3:
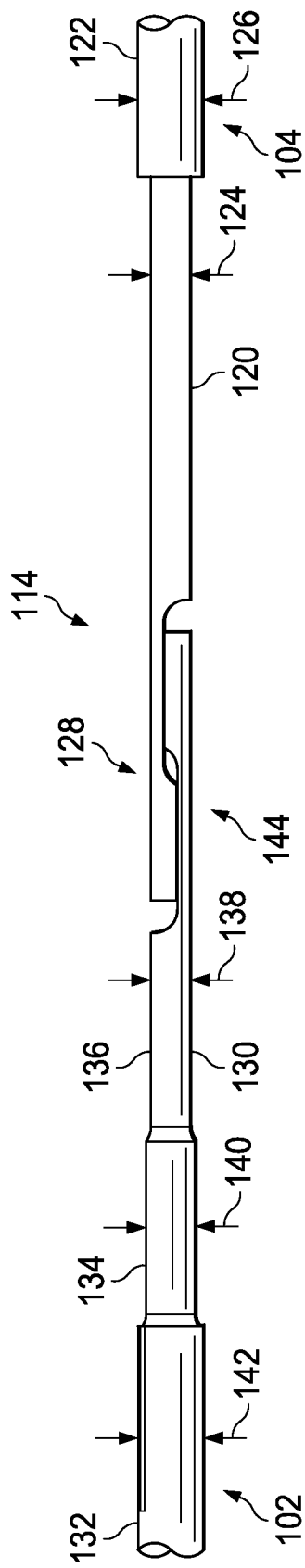
FIG. 3 is a side view of components of a transition section of an intravascular device according to an embodiment of the present disclosure.
Figure 7:
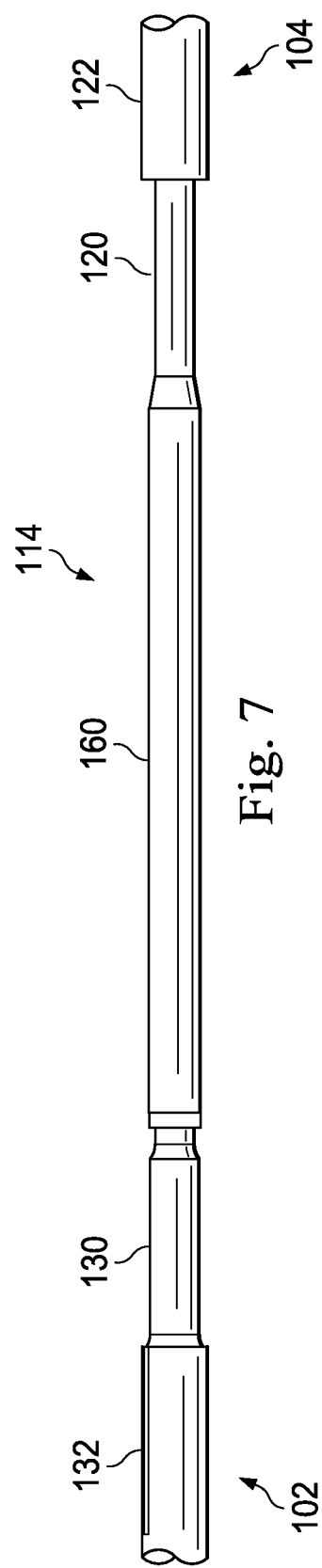
FIG. 7 is a side view of components of a transition section of an intravascular device according to an embodiment of the present disclosure.

Referring more specifically to FIG. 3, as shown, the distal portion 104 includes a core member 120 and a flexible element 122 according to an embodiment of the present disclosure. As shown, the core member 120 has an outer diameter 124 that is less than an outer diameter 126 of the flexible element 122. In some instances, the outer diameter 126 of the flexible element 122 is the same or substantially the same as the desired outer diameter of the intravascular device 100. Accordingly, in some particular embodiments the outer diameter 126 of the flexible element 122 is approximately 0.014", such as between 0.0138" and 0.0142". The flexible element 150 may be a coil, a polymer tubing, a coil-embedded polymer tubing, and/or combinations thereof. In that regard, the flexible element 150 may comprise multiple components in some implementations. Though not shown in FIG. 3, the distal portion 104 may also include a further flexible element extending distally from the component 108 (or a housing containing component 108) to the distal tip 105 of the intravascular device 100. Again, this distal flexible element may be a coil, a polymer tubing, and/or a coil-embedded polymer tubing. In some instances, the distal flexible element is radiopaque and/or includes a radiopaque tip. In some implementations, a flow sensor is positioned at the distal tip 105 of the intravascular device 100. Generally, the distal portion 104 of the intravascular device 100 may include features similar to those described in any of the patents and applications incorporated by reference above, but utilizing the transition sections of the present disclosure described below.

The core member 120 can be formed of any suitable material such as stainless steel, nickel and titanium alloys (such as Nitinol and NiTiCo), polyetheretherketone, 304V stainless steel, MP35N, or other metallic or polymeric materials. As discussed in greater detail below, a proximal section of the core member 120 includes an engagement structure 128 that allows the core member 120 to be coupled with a core member 130 of the central portion 102.

As also shown in FIG. 3, the central portion 102 includes a core member 130 and an outer layer 132 according to an embodiment of the present disclosure. As shown, the core member 120 includes section 134 and section 136 having different profiles. In particular, in the illustrated embodiment sections 134 and 136 have different outer diameters. In that regard, section 136 has an outer diameter 138 that is less than an outer diameter 140 of section 134. Similarly, the outer diameter 138 of section 136 is less than an outer diameter 142 of the outer layer 132. In some instances, the outer diameter 142 of the outer layer 132 is the same or substantially the same as the desired outer diameter of the intravascular device 100. Accordingly, in some particular embodiments the outer diameter 142 of the outer layer 132 is approximately 0.014", such as between 0.0138" and 0.0142".

The outer layer 132 includes conductors embedded therein. As discussed below, in the illustrated embodiments of the present disclosure, two conductors are embedded within the outer layer 132 of the central portion 102. In that regard, the conductors are fully encapsulated by the material forming the outer layer 132, which is a polymer in some instances. In some embodiments, an insulating layer—such as part of the outer layer 132 or a separate layer—is formed between the conductors and the core member 130. To that end, the insulating layer can be utilized to electrically isolate the conductors from the core member 130. As a result, each of the conductors embedded in the outer layer 132 and/or the core member 130 can be utilized as an independent electrical communication pathway of the intravascular device 100.

Each of the embedded conductors is formed of a conductive material, such as copper, gold, silver, platinum, or other suitable conductive material. Generally, the size of the conductors is selected to allow the conductors to be fully embedded within the material forming the outer layer 132. Accordingly, in some instances the conductor is between a 24 AWG conductor and a 64 AWG conductor, with some embodiments utilizing 48 AWG conductors. In other instances, larger or smaller conductors are utilized. In certain embodiments, the conductors are space substantially equally around a circumference of the central portion 102. However, the conductors may be embedded in any suitable manner and/or pattern, including symmetric, non-symmetric, geometric, and non-geometric patterns. In some instances, the conductors are conductive ribbons that allow for ease of connection and optimization of the coating wall thickness to maximize the core diameter.

The core member 130 can be formed of any suitable material such as stainless steel, nickel and titanium alloys (such as Nitinol and NiTiCo), polyetheretherketone, 304V stainless steel, MP35N, or other metallic or polymeric materials. A distal section of the core member 130 includes an engagement structure 144 that allows the core member 130 to be coupled with the core member 120 of the distal portion 104. Generally, the engagement structures 128 and 144 serve to provide a physical interface between the core members 120 and 130. In that regard, the engagement structures 128 and 144 can be utilized to facilitate transfer of torque, pushing forces, and/or pulling forces between the core members 120 and 130. Further, the engagement structures 128 and 144 can be utilized to align the core member 120 and 130 with respect to each other in one, two, or three dimensions. Accordingly, the engagement structures 128 and 144 may include any combination of structural features to facilitate such alignment, including without limitation projections, recesses, flats, tapers, curves/arcs, bends, locking features, and/or combinations thereof.

Figure 4:
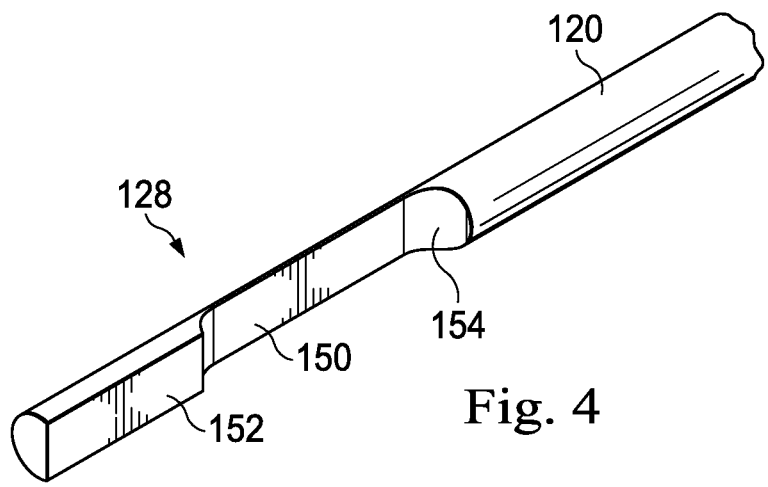
FIG. 4 is a perspective view of an engagement structure of a core component according to an embodiment of the present disclosure.
Figure 5:
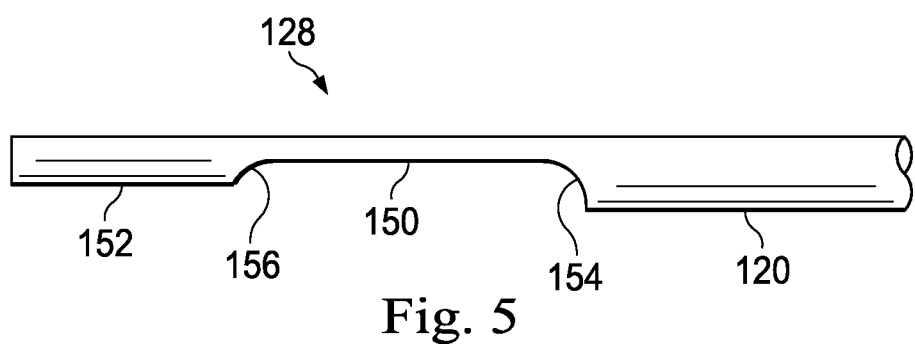
FIG. 5 is a side view of the engagement structure of the core component of FIG. 4.
Figure 6:
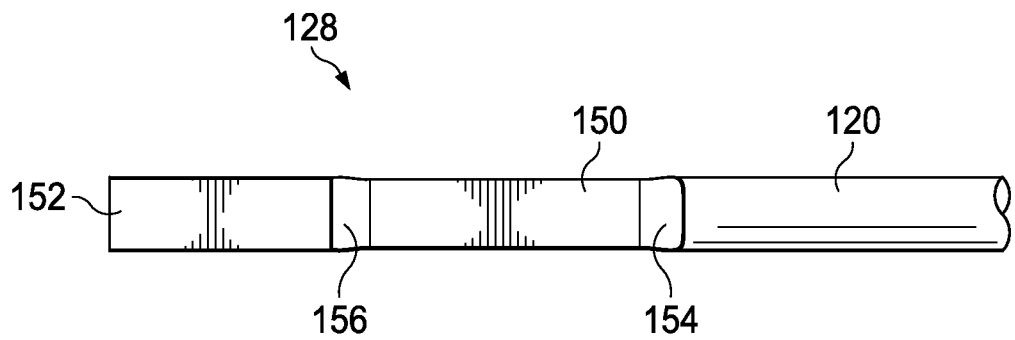
FIG. 6 is a bottom view of the engagement structure of the core component of FIGS. 4 and 5.
Figure 9:
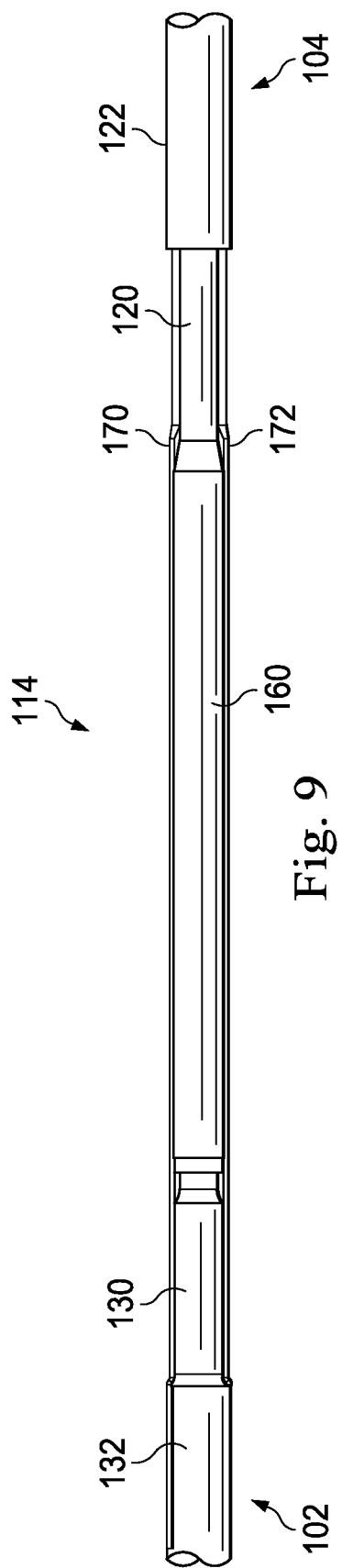
FIG. 9 is a side view of components of a transition section of an intravascular device according to an embodiment of the present disclosure.

Referring now to FIGS. 4-6, shown therein are aspects of the engagement structure 128 according to the present disclosure. In the illustrated embodiments of the present disclosure, the engagement structures 128 and 144 have the same structural features and, therefore, engagement structure 144 will not be described separately. However, in other embodiments the engagement structures 128 and 144 have different structural features configured to mate with one another. As shown, the engagement structure 128 includes a flat 150 and a flat 152 that are staggered from one another. In that regard, flat 150 is recessed a greater extent than flat 150. For example, in the illustrated embodiment flat 150 is positioned approximately 33% of the way through the core member 120, whereas flat 152 is positioned approximately 67% of the way through the core member 120. The engagement structure 128 also includes a transition 154 between the flat 150 and the outer surface of the core member 120. Similarly, the engagement structure 128 includes a transition 156 between the flat 150 and the flat 152. In the illustrated embodiment, the transitions 154 and 156 are curved or arcuate, but in other instances are tapered and/or stepped. In some instances, the engagement structure 128 is defined in the core member 120 by removing portions of the core member utilizing a suitable manufacturing technique, such as grinding, etching, laser ablation, and/or combinations thereof. In other instances, the engagement structure 128 is defined in the core member 120 as part of a molding process.

Referring again to FIG. 3, to couple the central portion 102 to the distal portion 104 the engagement structures 128 and 144 are engaged with one another. In particular, the flats 150 and 152 of the engagement structure 128 are engaged with corresponding flats of the engagement structure 144, as shown. Further, in order to provide the desired alignment in the axial direction the central portion 102 and the distal portion 104 can be pulled away from each other such that the transition 156 of the engagement structure 128 engages a corresponding transition of the engagement structure 144. With the core members 120 and 130 engaged via the engagement structures 128 and 144, a tubular member 160 can be positioned around the engagement structures 128 and 144 to help maintain the relative positions of the core members 120 and 130. The tubular member 160 can be formed of any suitable material, including metals and polymers, including without limitation 304V Stainless Steel, Nitinol, NiTiCo, and Polyimide. In some instances, the tubular member 160 is a hypotube. Solder or adhesive can be flown into the interior of the tubular member 160 to fixedly secure the core members 120 and 130 to one another and to the tubular member 160. In that regard, the solder or adhesive will fill the gaps between the core members 120 and 130 and surround the core members 120 and 130 within the tubular member 160 to provide a solid physical connection between the components.

As shown in FIGS. 8A and 8B, the tubular member 160 can be initially placed around the core member 120 at a position distal of the engagement structure 128 to allow the engagement structures 128 and 144 to engage one another. Once the engagement structures 128 and 144 are engaged, the tubular member 160 can be translated proximally along core member 120, as shown by arrow 162, to a position surrounding the engaged engagement structures 128 and 144. With the tubular member 160 positioned around the engagement structures 128 and 144, the core members 120 and 130 can be joined together using solder and/or adhesive. As noted above, in some instances it is advantageous to provide slight tension to the core members 120 and 130 (e.g., by pulling them apart) when coupling them together. Note that a similar approach can be utilized where the tubular member begins around core member 130 proximal of engagement structure 144 and is then translated distally to surround the engaged engagement structures 128 and 144. Further, it should be noted that the core member 120 and 130 can be secured to one another by solder, adhesive, welding, etc. without the tubular member 160 positioned around the engagement structures. Further, in some embodiments the intravascular device 100 does not include tubular member 160, but may include other element(s) or structure(s) to solidify the joint.

Referring now to FIG. 9-13, electrical conductors 170 and 172 of the distal portion 104 have been electrically coupled to the embedded conductors in the outer layer 132 of the central portion 102. In some embodiments, an insulating layer is formed around the core members 120 and 130 and the tubular member 160 prior to extending the electrical conductors 170 and 172 over the exposed portions of the core members 120 and 130 and the tubular member 160 for connection to the embedded conductors. In that regard, the insulating layer serves to electrically isolate the core members 120 and 130 and the tubular member 160 from the conductors 170 and 172. The insulating layer may be formed of any suitable material. In some instances, the insulating layer is a polymer layer. In some implementations, the insulating layer is a parylene layer. Generally, the insulating layer may have any suitable thickness, but in some instances has a thickness between about 0.0001" and about 0.001". In some instances, the conductors 170 and 172 are coated with an insulating layer in addition to or in lieu of the insulating layer around the core member 120 and 130 and the tubular member 160.

As shown in FIGS. 10 and 11, the tubular member 160 includes flattened portions to allow the conductors 170 and 172 to extend along the outside of the tubular member 160 without increasing the outer diameter of the transition section 114 beyond the desired outer diameter of the intravascular device 100. For similar reasons, in some instances the conductors 170 and 172 have a rectangular, oval, rounded rectangular profile, and/or flattened profile. As shown in FIG. 10, the conductor 170 extends a long a flat 174 of the tubular member 160 and is electrically coupled to an embedded conductor of the central portion 102 at connection 176. The conductors 170 can be electrically coupled to the embedded conductor using any suitable techniques, including without limitation solder, physical contact, an electric coupler, etc. Similarly, as shown in FIG. 11, the conductor 172 extends a long a flat 178 of the tubular member 160 and is electrically coupled to an embedded conductor of the central portion 102 at connection 180. The conductors 172 can be electrically coupled to the embedded conductor using any suitable techniques, including without limitation solder, physical contact, an electric coupler, etc.

Figure 12:
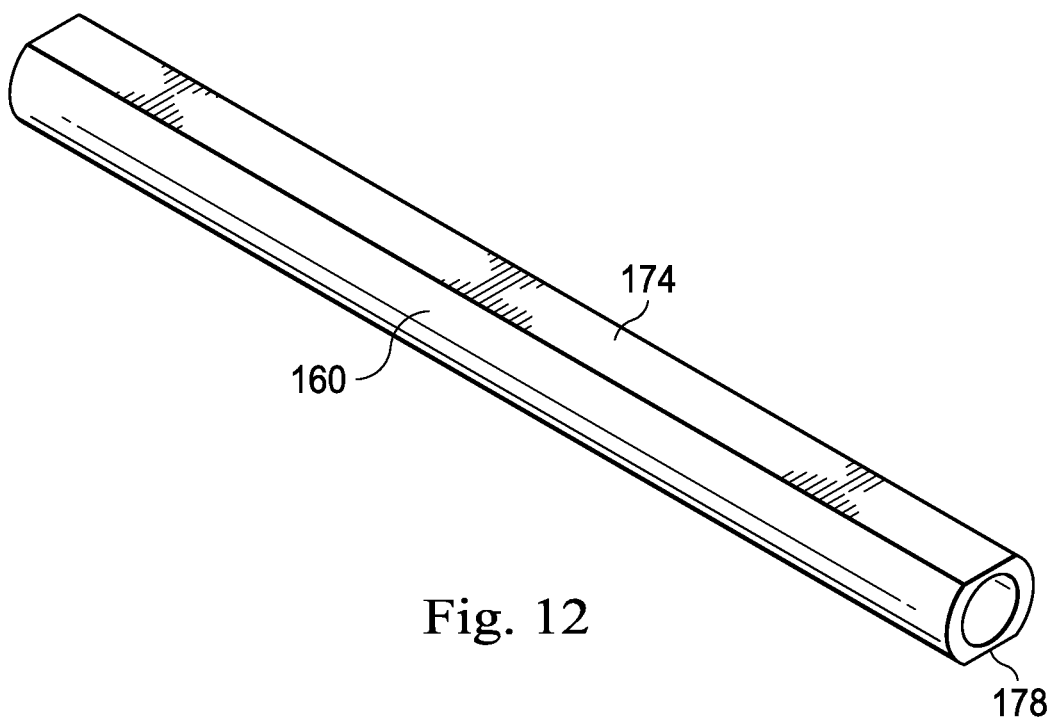
FIG. 12 is a perspective view of a component of a transition section of an intravascular device according to an embodiment of the present disclosure.
Figure 13:
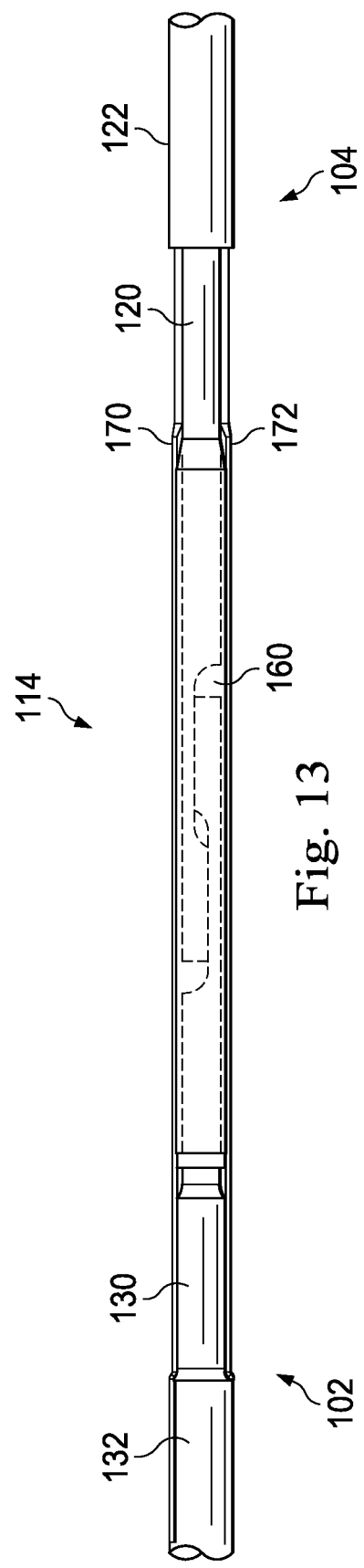
FIG. 13 is a side view of components of a transition section of an intravascular device according to an embodiment of the present disclosure.

In some implementations, the embedded conductors are exposed for electrical coupling to conductors 170 and 172 by removing a portion of the outer layer 132 covering the embedded conductors for a certain length along the longitudinal axis of the central portion 102. In some implementations, the embedded conductors are exposed for electrical coupling to conductors 170 and 172 at an end surface extending perpendicular to the longitudinal axis of the central portion 102. That is, the embedded conductors are not exposed along the length of the central portion, but rather are exposed at an end surface of the outer layer 132. FIG. 12 provides a perspective view of the tubular member 160 that shows the flats 174 and 178. FIG. 13 provides a side view of the transition section 114 showing the engagement of the core members 120 and 130 within the tubular member 160 and the conductors 170 and 172 extending over the tubular member 160.

Figure 14:
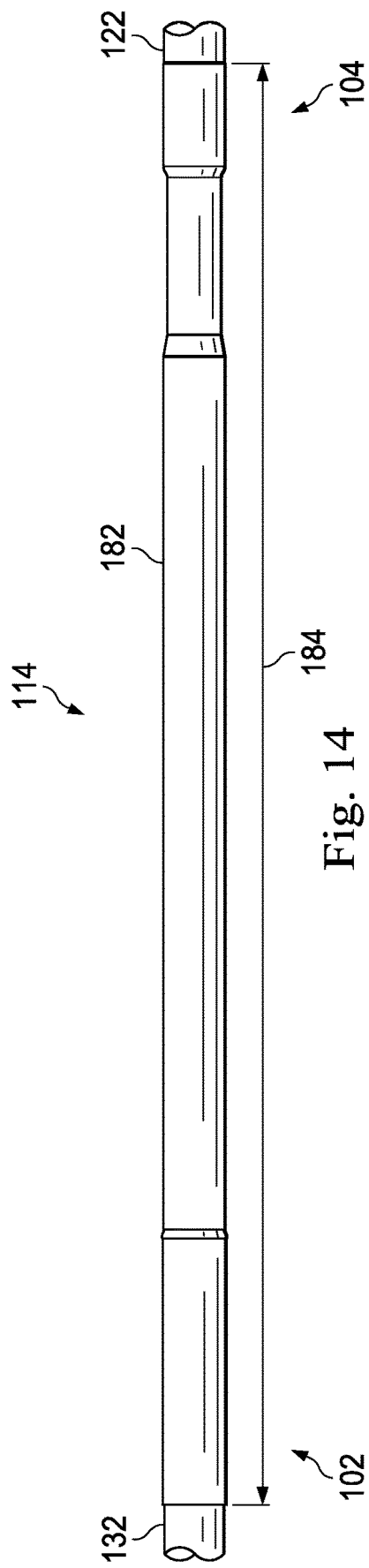
FIG. 14 is a side view of components of a transition section of an intravascular device according to an embodiment of the present disclosure.

Referring now to FIG. 14, an outer layer 182 is formed over the conductors 170, 172, the tubular member 160, and the core members 120 and 130. In the illustrated embodiment, the outer layer 182 extends along the length of the intravascular device 100 between the central portion 102 and the distal portion 104 a distance 184. As shown, the distance 184 results in the outer layer 182 covering the transition section 114 and portions of each of the flexible element 122 of the distal portion 104 and the outer layer 132 of the central portion 102. The outer layer 182 may cover a lesser amount of the transition section 114 and/or greater or lesser amounts of the central portion 102 and/or the distal portion 104 in other instances. The outer layer 182 can be formed of any suitable material. In some instances, the outer layer 182 is a polymer material configured to seal the transition section 114. The outer layer 182 is a PET shrink fit tubing in some instances. An adhesive is placed inside the PET shrink fit tubing to ensure adequate moisture barrier for the electrical connections in some implementations. In some instances, a coating is provided on at least a portion of the intravascular device 100, which may include the transition section 114. In that regard, the coating can be a suitable hydrophilic or hydrophobic coating. In some implementations, the coating provides increased lubricity. Exemplary coating materials include, without limitation, PTFE impregnated polyimide, silicone-based coatings, and hydrophilic based coatings. Generally, the coating will be a very thin layer of material. For example, in some implementations the coating has a thickness less than about 0.0005", less than about 0.0001", and/or less than about 0.00005".

Figure 15:
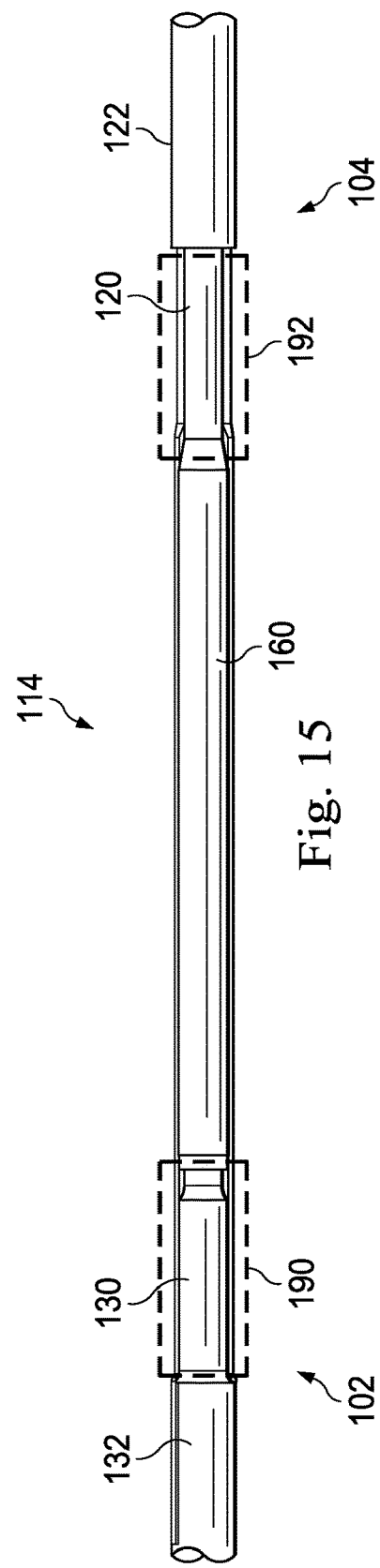
FIG. 15 is a side view of components of a transition section of an intravascular device according to an embodiment of the present disclosure.

Referring now to FIG. 15, in some instances the transition section 114 include a tubular member 190 and/or a tubular member 192. In that regard, the tubular members 190 and 192 can be utilized to increase the diameter of the transition section 114 in the areas surrounding the core members 120 and/or 130. In that regard, in order to allow the tubular member 160 to translate along the length of the core member 120 to facilitate engagement of the core members 120 and 130 prior to the tubular member 160 being positioned around the engaged engagement structures 128 and 144, a portion of the core member 120 having a reduced outer diameter relative to the flexible element 122 and the tubular member 160 will be exposed between the flexible element 122 and the tubular member 160. Similarly, a portion of the core member 130 having a reduced outer diameter relative to the tubular member 160 and the outer layer 132 may be exposed between the tubular member 160 and the outer layer 132. Accordingly, tubular members 190 and 192 may be utilized to increase the diameters in these areas to reduce the overall variability in the outer diameter of the transition section 114. In some instances, the tubular members are polymer tubings. In some implementations, the tubing is slit to allow for positioning over the core member 130 after positioning the tubular member 160. In some particular embodiments, the tubular members 190 and 192 are PET shrink fit tubings. In some instances, only one of the tubular members 190 and 192 is utilized.

The guide wires of the present disclosure can be connected to an instrument, such as a computing device (e.g. a laptop, desktop, or tablet computer) or a physiology monitor, that converts the signals received by the sensors into pressure and velocity readings. The instrument can further calculate Coronary Flow Reserve (CFR) and Fractional Flow Reserve (FFR) and provide the readings and calculations to a user via a user interface. In some embodiments, a user interacts with a visual interface to view images associated with the data obtained by the intravascular devices of the present disclosure. Input from a user (e.g., parameters or a selection) are received by a processor in an electronic device. The selection can be rendered into a visible display.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclo-

What is claimed is:

1. A sensing guide wire, comprising:
a proximal assembly having a proximal core member, at least one proximal electrical conductor, a connector in electrical communication with the at least one proximal electrical conductor, and a proximal outer layer encapsulating at least a portion of the at least one proximal electrical conductor, wherein the proximal core member includes a first end section, wherein the proximal outer layer insulates the at least one proximal electrical conductor from the proximal core member;
a distal assembly different from the proximal assembly, and coupled to the proximal assembly, the distal assembly having a distal core member, a sensing element, and at least one distal electrical conductor different from the proximal electrical conductor and coupled to the sensing element, wherein the distal core member includes a second end section, and wherein the proximal assembly and distal assembly are connected together such that:
the second end section of the distal core member is coupled to the first end section of the proximal core member at a first location, and the at least one distal electrical conductor is coupled to the at least one proximal electrical conductor at a second location to establish electrical communication between the connector and the sensing element via the at least one distal electrical conductor and the at least one proximal electrical conductor, wherein the first location and the second location are proximate to one another; and
a tubular member positioned around the first and second end sections such that an intermediate portion of the guide wire includes the first and second end sections and the tubular member.

2. The guide wire of claim 1, wherein the sensing element includes at least one of a pressure sensor or a flow sensor.

3. The guide wire of claim 1, wherein the tubular member is a hypotube.

4. The guide wire of claim 3, wherein the hypotube includes at least one flat.

5. The guide wire of claim 4, wherein the at least one distal electrical conductor extends along the at least one flat of the hypotube.

6. The guide wire of claim 4, wherein the hypotube includes two flats, wherein the at least one distal electrical conductor includes two distal electrical conductors, and wherein the two distal electrical conductors extend along the two flats of the hypotube.

7. The guide wire of claim 1, wherein each of the proximal core member and the distal core member is formed of at least one of 304V Stainless Steel, Nitinol, NiTiCo, and MP35N®.

8. The guide wire of claim 7, wherein the distal core member is formed of a different material than the proximal core member.

9. The guide wire of claim 1, wherein the distal assembly includes a first flexible element proximal of the sensing element and a second flexible element distal of the sensing element.

10. The guide wire of claim 9, wherein the first flexible element includes at least one of a coil and a polymer tubing.

11. The guide wire of claim 10, wherein the second flexible element includes at least one of a coil and a polymer tubing.

12. The guide wire of claim 1, further comprising an insulating coating extending over the portion of the guide wire that includes the first and second end sections, and the tubular member.

13. The guide wire of claim 1, wherein the guide wire has an outer diameter of approximately 0.014", 0.018", or 0.035".

14. The guide wire of claim 1, wherein the proximal outer layer comprises a polymer material.

15. The guide wire of claim 1, wherein the proximal core member comprises a first region distal to the proximal outer layer and a second region distal to the first region, wherein the second region comprises a first diameter, the first region comprises a second diameter greater than the first diameter, and the proximal outer layer comprises a third diameter greater than the second diameter, wherein the first end section forms part of the second region.

16. The guide wire of claim 1, wherein the first end section comprises a distal engagement structure, and wherein the second end section comprises a proximal engagement structure engaged with the distal engagement structure.

17. The guide wire of claim 16, wherein the distal engagement structure includes a flat that is engaged with a flat of the proximal engagement structure.

18. The guide wire of claim 16, wherein the distal engagement structure includes a projection that is engaged with a recess of the proximal engagement structure.

19. The guide wire of claim 1, wherein the at least one distal electrical conductor is electrically coupled to the at least one proximal electrical conductor through a removed section of the proximal outer layer.

20. The guide wire of claim 19, wherein the first and second end sections are fixedly secured to one another within the tubular member by at least one of a solder or adhesive.

21. A method of forming a sensing guide wire, the method comprising:
providing a proximal assembly having a proximal core member, at least one proximal electrical conductor, a connector in electrical communication with the at least one proximal electrical conductor, and a proximal outer layer encapsulating at least a portion of the at least one proximal electrical conductor, wherein the proximal core member includes a first end section, wherein the proximal outer layer insulates the at least one proximal electrical conductor from the proximal core member;
providing a distal assembly different from the proximal assembly, and having a distal core member, a sensing element, and at least one distal electrical conductor different from the proximal electrical conductor, and coupled to the sensing element, wherein the distal core member includes a second end section; and
coupling the proximal assembly to the distal assembly, including:
securing the proximal core member to the distal core member, wherein securing the proximal core member to the distal core member includes coupling the first end section and the second end section at a first location;
coupling the at least one distal electrical conductor to the at least one proximal electrical conductor at a second location such that the connector is in electrical communication with the sensing element via the at least one distal electrical conductor and the at least one proximal electrical conductor, wherein the first location and the second location are proximate to one another; and positioning a tubular member around the first and second end sections such that an intermediate portion of the guide wire includes the first and second end sections and the tubular member.

\* \* \* \* \*